United States Patent
Cottrell

(10) Patent No.: US 6,201,010 B1
(45) Date of Patent: Mar. 13, 2001

(54) ANTICONVULSANT DERIVATIVES USEFUL IN LOWERING BLOOD PRESSURE

(75) Inventor: Sandra C. Cottrell, Doylestown, PA (US)

(73) Assignee: Ortho-McNeil Pharmceutical, Inc., Raritan, NJ (US)

( * ) Notice: Subject to any disclaimer, the term of this patent is extended or adjusted under 35 U.S.C. 154(b) by 0 days.

(21) Appl. No.: 09/538,182

(22) Filed: Mar. 30, 2000

Related U.S. Application Data

(60) Provisional application No. 60/128,400, filed on Apr. 8, 1999.

(51) Int. Cl.[7] .................................................... A61K 31/35
(52) U.S. Cl. ........................................ 514/454; 514/554
(58) Field of Search ..................................... 514/454, 554

(56) References Cited

U.S. PATENT DOCUMENTS 6,071,537 * 6/2000 Shank .................................. 424/464

* cited by examiner

*Primary Examiner*—Theodore J. Criares
*Assistant Examiner*—Jennifer Kim
(74) *Attorney, Agent, or Firm*—Ralph R. Palo

(57) ABSTRACT

Anticonvulsant derivatives useful in lowering blood pressure in overweight individuals.

3 Claims, No Drawings

ANTICONVULSANT DERIVATIVES USEFUL IN LOWERING BLOOD PRESSURE

This application claims benefit of provisional application 60/128,400 Apr. 8, 1999.

BACKGROUND OF THE INVENTION

Compounds of Formula I:

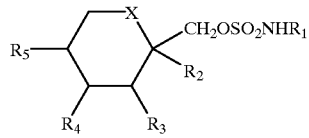

are structurally novel antiepileptic compounds that are highly effective anticonvulsants in animal tests (Maryanoff, B. E., Nortey, S. O., Gardocki, J. F., Shank, R. P. and Dodgson, S. P. *J. Med. Chem.* 30, 880–887, 1987; Maryanoff, B. E., Costanzo, M. J., Shank, R. P., Schupsky, J. J., Ortegon, M. E., and Vaught J. L. Bioorganic & Medicinal Chemistry Letters 3, 2653–2656, 1993). These compounds are covered by U.S. Pat. No. 4,513,006. One of these compounds 2,3:4,5-bis-O-(1-methylethylidene)-β-D-fructopyranose sulfamate known as topiramate has been demonstrated in clinical trials of human epilepsy to be effective as adjunctive therapy or as monotherapy in treating simple and complex partial seizures and secondarily generalized seizures (E. FAUGHT, B. J. WILDER, R. E. RAMSEY, R. A. REIFE, L D. KRAMER, G. W. PLEDGER, R. M. KARIM et. al., Epilepsia 36 (S4) 33, 1995; S. K. SACHDEO, R. C. SACHDEO, R. A. REIFE, P. LIM and G. PLEDGER, Epilepsia 36 (S4) 33, 1995), and is currently marketed for the treatment of simple and complex partial seizure epilepsy with or without secondary generalized seizures in approximately twenty countries including the United States, and applications for regulatory approval are presently pending in several additional countries throughout the world.

Compounds of Formula I were initially found to possess anticonvulsant activity in the traditional maximal electroshock seizure (MES) test in mice (SHANK, R. P., GARDOCKI, J. F., VAUGHT, J. L., DAVIS, C. B., SCHUPSKY, J. J., RAFFA, R. B., DODGSON, S. J., NORTEY, S. O., and MARYANOFF, B. E., Epilepsia 35 450–460, 1994). Subsequent studies revealed that Compounds of Formula I were also highly effective in the MES test in rats. More recently topiramate was found to effectively block seizures in several rodent models of epilepsy (J. NAKAMURA, S. TAMURA, T. KANDA, A. ISHII, K. ISHIHARA, T. SERIKAWA, J. YAMADA, and M. SASA, Eur. J. Pharmacol. 254 83–89, 1994), and in an animal model of kindled epilepsy (A. WAUQUIER and S. ZHOU, Epilepsy Res. 24, 73–77, 1996).

Clinical studies on topiramate have revealed previously unrecognized pharmacological properties which suggest that topiramate will be effective in lowering blood pressure, both systolic and disstolic, in humans, particularly in overweight individuals.

DISCLOSURE OF THE INVENTION

Accordingly, it has been found that compounds of the following formula I:

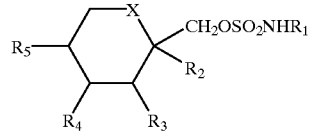

wherein X is O or $CH_2$, and R1, R2, R3, R4 and R5 are as defined hereinafter are useful in maintaining weight loss.

DETAILED DESCRIPTION OF THE PREFERRED EMBODIEMENTS

The sulfamates of the invention are of the following formula (I):

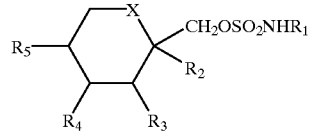

wherein

X is $CH_2$ or oxygen; $R_1$ is hydrogen or alkyl; and $R_2$, $R_3$, $R_4$ and $R_5$ are independently hydrogen or alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

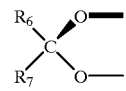

wherein $R_6$ and $R_7$ are the same or different and are hydrogen, lower alkyl or are alkyl and are joined to form a cyclopentyl or cyclohexyl ring.

$R_1$ in particular is hydrogen or alkyl of about 1 to 4 carbons, such as methyl, ethyl and iso-propyl. Alkyl throughout this specification includes straight and branched chain alkyl. Alkyl groups for $R_2$, $R_3$, $R_4$, $R_5$, $R_6$ and $R_7$ are of about 1 to 3 carbons and include methyl, ethyl, iso-propyl and n-propyl. When X is $CH_2$, $R_4$ and $R_5$ may combine to form a benzene ring fused to the 6-membered X-containing ring, i.e., $R_4$ and $R_5$ are defined by the alkatrienyl group =C—CH=CH—CH=.

A particular group of compounds of formula (I) is that wherein X is oxygen and both $R_2$ and $R_3$ and $R_4$ and $R_5$ together are methylenedioxy groups of the formula (II), wherein $R_6$ and $R_7$ are both hydrogen both alkyl or combine to form a spiro cyclopentyl or cyclohexyl ring, in particular where $R_6$ and $R_7$ are both alkyl such as methyl. A second group of compounds is that wherein X is $CH_2$ and $R_4$ and $R_5$ are joined to form a benzene ring. A third group of compounds of formula (I) is that wherein both $R_2$ and $R_3$ are hydrogen.

The compounds of formula (I) may be synthesized by the following methods:

(a) Reaction of an alcohol of the formula $RCH_2OH$ with a chlorosulfamate of the formula $CISO_2NH_2$ or $CISO_2NHR_1$ in the presence of a base such as potassium a-butoxide or sodium hydride at a temperature of about −20° to 25° C. and in a solvent such as toluene, THF or dimethylformamide wherein R is a moiety of the following formula (III):

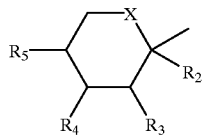

(b) Reaction of an alcohol of the formula $RCH_2OH$ with sulfurylchloride of the formula $SO_2Cl_2$ in the presence of a base such as triethylamine or pyridine at a temperature of about −40° to 25° C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R_1NH_2$ at a temperature of abut 40° to 25° C. in a solvent such as methylene chloride or acetonitrile to produce a compound of formula (I). The reaction conditions for (b) are also described by T. Tsuchiya et al. in Tet. Letters, No. 36, p. 3365 to 3368 (1978).

(c) Reaction of the chlorosulfate $RCH_2OSO_2Cl$ with a metal azide such as sodium azide in a solvent such as methylene chloride or acetonitrile yields an azidosulfate of the formula $RCH_2OSO2N_3$ as described by M. Hedayatullah in Tet. Lett. p. 2455–2458 (1975). The azidosulfate is then reduced to a compound of formula (I) wherein $R_1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R_2$ and $R_3$ and $R_4$ and $R_5$ are identical and are of the formula (II) may be obtained by the method of R. F. Brady in Carbohydrate Research, Vol. 14, p. 35 to 40 (1970) or by reaction of the trimethylsilyl enol ether of a $R_6COR_7$ ketone or aldehyde with fructose at a temperature of about 25° C., in a solvent such a halocarbon, e.g. methylene chloride in the presence of a protic acid such as hydrochloric acid or a Lewis Acid such as zinc chloride. The trimethylsilyl enol ether reaction is described by G. L. Larson et al in J. Org. Chem. Volaa 38, No. 22, p. 3935 (1973).

Further, carboxylic acids and aldehydes of the formulae RCOOH and RCHO may be reduced to compounds of the formula RCH2OH by standard reduction techniques, e.g. reaction with lithium aluminum hydride, sodium borohydride or borane-THF complex in an inert solvent such a diglyme, THF or toluene at a temperature of about 0° to 100° C., e.g. as described by H. O. House in "Modern Synthetic Reactions", 2nd Ed., pages 45 to 144 (1972).

The compounds of formula I: may also be made by the process disclosed in U.S. Pat. No. 5,387,700, which is incorporated by reference herein.

The compounds of formula I include the various individual isomers as well as the racemates thereof, e.g., the various alpha and beta attachments, i.e., below and above the plane of the drawing, of $R_2$, $R_3$, $R_4$ and $R_5$ on the 6-membered ring. Preferably, the oxygene of the methylenedioxy group (II) are attached on the same side of the 6-membered ring.

In a retrospective analysis of the topiramate safety database, mean decreases in systolic and diastolic blood pressure of 3.8 mmHg and 2.6 mmHg, respectively, were observed in all subjects (n=1160). Those subjects with weight at baseline in excess of 100 kg (n=114) had greater decreases of 4.0 mmHg and 3.5 mmHg, respectively. In subjects with both abnormally high blood pressure (defined as ≧140 mmHg systolic or ≧90 mmHg diastolic) and weight in excess of 100 kg (n=39), systolic and diastolic blood pressure decreased by 11.6 mmHg and 8.5 mmHg, respectively.

For lowering blood pressure, a compound of formula (I) may be employed at a daily dose in the range of about 100 mg to 400 mg, usually in two daily divided doses, for an average adult human. A unit dose would contain about 15 to 200 mg of the active ingredient.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable solutions may also be prepared in which case appropriate stabilizing agents may be employed. Topiramate is currently available for oral administration in round tablets containing 25 mg, 100 mg or 200 mg of active agent. The tablets contain the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

The pharmaceutical compositions herein will contain, per dosage unit, e.g., tablet, capsule, powder injection, teaspoonful, suppository and the like from about 25 to about 200 mg of the active ingredient.

What is claimed is:

1. A method for lowering blood pressure in mammals, comprising administering to such a mammal a therapeutically effective amount for treating such condition of a compound of the formula I:

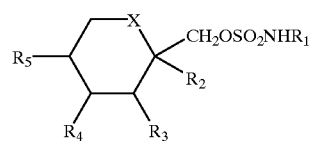

wherein
X is $CH_2$ or oxygen;
$R_1$ is hydrogen or alkyl; and
$R_2$, $R_3$, $R_4$ and $R_5$ are independently hydrogen or alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

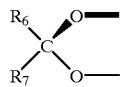

wherein $R_6$ and $R_7$ are the same or different and are hydrogen, or alkyl and are joined to form a cyclopentyl or cyclohexyl ring.

2. The method of claim 1 wherein the compound of formula I is topiramate.

3. The method of claim 1, wherein the therapeutically effective amount is of from about 100 to 400 mg/day.

* * * * *